(12) United States Patent
Tsuruoka et al.

(10) Patent No.: US 9,877,960 B2
(45) Date of Patent: Jan. 30, 2018

(54) LEARNING AND MEMORY IMPROVER

(71) Applicants: SUNTORY HOLDINGS LIMITED, Osaka (JP); CEREBOS PACIFIC LIMITED, China Square Central (SG)

(72) Inventors: Nobuo Tsuruoka, Osaka (JP); Hiroshi Watanabe, Osaka (JP)

(73) Assignees: SUNTORY HOLDINGS LIMITED, Osaka (JP); CEREBOS PACIFIC LIMITED, China Square Central (SG)

( * ) Notice: Subject to any disclaimer, the term of this patent is extended or adjusted under 35 U.S.C. 154(b) by 0 days.

(21) Appl. No.: 14/646,182

(22) PCT Filed: Nov. 21, 2013

(86) PCT No.: PCT/JP2013/081371
§ 371 (c)(1),
(2) Date: May 20, 2015

(87) PCT Pub. No.: WO2014/080973
PCT Pub. Date: May 30, 2014

(65) Prior Publication Data
US 2015/0297584 A1 Oct. 22, 2015

(30) Foreign Application Priority Data

Nov. 21, 2012 (JP) ................................. 2012-255047

(51) Int. Cl.
*A61K 31/495* (2006.01)

(52) U.S. Cl.
CPC ................................. *A61K 31/495* (2013.01)

(58) Field of Classification Search
CPC .................................................. A61K 31/495
See application file for complete search history.

(56) References Cited

U.S. PATENT DOCUMENTS

| 5,091,427 A | 2/1992 | Nickel et al. |
| 6,518,235 B1 | 2/2003 | Oomura et al. |
| 2012/0282387 A1 | 11/2012 | Matsubayashi et al. |
| 2012/0283178 A1 | 11/2012 | Tsuruoka et al. |
| 2012/0283270 A1 | 11/2012 | Matsubayashi et al. |

FOREIGN PATENT DOCUMENTS

| JP | 02-115175 | 4/1990 | | |
| JP | 11-279074 | 10/1999 | | |
| JP | 2003-221337 | 8/2003 | | |
| JP | 2008-255087 | 10/2008 | | |
| JP | 2011-136916 | 7/2011 | | |
| JP | 2011-213700 | 10/2011 | | |
| JP | 2012-517214 | 8/2012 | | |
| JP | 2012-517998 | 8/2012 | | |
| JP | 2012-246224 | 12/2012 | | |
| WO | WO 2011077760 A1 | * | 6/2011 | ........... A61K 31/496 |
| WO | 2012/160713 | 11/2012 | | |
| WO | WO 2012160713 A1 | * | 11/2012 | ........... A61K 31/495 |

OTHER PUBLICATIONS

Brands World Jul. 8-Aug. 2012, p. 1.*
Tsi, D.,"Clinical study on the combined effect of capsaicin, green tea extract and essence of chicken on body fat content in human subjects." Journal of nutritional science and vitaminology 49.6 (2003): 437-441.*
Tsuruoka, N., "A DKP cyclo (L-Phe-L-Phe) found in chicken essence is a dual inhibitor of the serotonin transporter and acetylcholinesterase." PloS one 7.11 (2012): e50824.*
Stedman, T.L., Stedman's concise medical dictionary for the health professions. Lippincott Williams & Wilkins, 2001.; accessed online at http://www.stedmansonline.com/popup.aspx?aid=5161130 on Jun. 9, 2016.*
Nobutaka, D. O. E., "Behavioral despair during a water maze learning task in mice." Experimental animals 59.2 (2010): 191-197.*
International Search Report for PCT/JP2013/081371, dated Feb. 25, 2014.
Toda et al., "Development of an Efficient Therapeutic Agent for Alzheimer's Disease: Design and Synthesis of Dual Inhibitors of Acetylcholinesterase and Serotonin Transporter", *Chem. Pharm. Bull.* 58(3): 273-287 (2010).
Taiwanese Office Action issued in TW Patent Application No. 102142450 dated Jan. 16, 2017.
"Guidelines for Prevention and Treatment of Senile Dementia," pp. 83-86, Editors: Zhiyuan Yu et al., People's Medical Publishing House (Jan. 2000), along with a partial English language translation.
"A wonderful life like red sunset: psychological health and health care of the elderly friends," pp. 216-221, Editor: Shuo Li, Ancient Chinese Medicine Books Press (Aug. 2012), along with a partial English language translation.
Chinese Office Action issued in CN Patent Application No. 201380071017.X dated Mar. 28, 2017, along with an English language translation.

* cited by examiner

*Primary Examiner* — Matt Mauro
(74) *Attorney, Agent, or Firm* — Greenblum & Bernstein, P.L.C.

(57) ABSTRACT

The present invention aims to provide antidementia agents which are free from the problem of side effects and are excellent in safety. The present invention also aims to provide agents for improving learning and memory which are useful for improvement of learning and memory and can be ingested continuously. The present invention provides antidementia agents and agents for improving learning and memory, each comprising a cyclic dipeptide with the 2,5-diketopiperazine structure as an active ingredient.

6 Claims, 2 Drawing Sheets

LEARNING AND MEMORY IMPROVER

TECHNICAL FIELD

The present invention relates to an antidementia agent and an agent for improving learning and memory. In particular, the present invention relates to an antidementia agent and an agent for improving learning and memory which comprise 2,5-piperazinedione,3,6-bis(phenylmethyl)-,(3S,6S) as an active ingredient.

BACKGROUND ART

As the human life span has lengthened, dementia is becoming an important problem in a modern society. Dementia refers to a state in which daily life is disrupted continuously due to various disorders induced by death or impaired activity of brain cells due to various causes. The most common cause of dementia is degenerative disease in which cerebral nerve cells gradually die, and the second common cause is cerebrovascular dementia.

Examples of degenerative disease include Alzheimer's disease, frontotemporal dementia, dementia with Lewy bodies, etc. On the other hand, cerebrovascular dementia is caused by death of cerebral nerve cells or destruction of the network of nerves triggered by cerebral infarction, cerebral hemorrhage, cerebral arteriosclerosis, etc. Examples of symptoms which are directly caused by destruction of cerebral nerve cells include memory disorder, disorientation, impairment of the ability to understand and judge, impairment of executive function, etc.

Although the cause of Alzheimer's disease, which is a typical example of degenerative disease, is not well understood, since the level of acetylcholine, which is a neurotransmitter, in the patient's brain is decreased, it is considered that reduced function of cholinergic nerves is one of the causes of Alzheimer's disease. Hence, a mainstream method for the treatment of Alzheimer's disease is a method which is aimed at preventing reduced function of cholinergic nerves by increasing the concentration of acetylcholine. Specifically, in response to a decrease of acetylcholine in the patient's brain, the activity of acetylcholine esterase (AChE), which is an enzyme that decomposes acetylcholine, is inhibited so that decomposition of acetylcholine is reduced to thereby relatively increase the concentration of acetylcholine. It is known that the above method cannot treat the symptoms completely but can improve the symptoms or retard the progress of the symptoms. Currently, tacrine, donepezil (Aricept), rivastigmine and galanthamine, all of which exhibit AChE inhibitory action, are commercially available as agents for treating Alzheimer's disease (Non-Patent Document 1). However, since tacrine has strong side effects such as hepatotoxicity, there is a problem that long-term administration of tacrine is not possible. On the other hand, donepezil has fewer side effects than those of tacrine but is reported to have side effects such as vomition, decreased appetite/anorexia, and diarrhea (Non-Patent Document 2).

It is reported that 40 to 50% of patients with Alzheimer's disease had depressed mood and that 10 to 20% had depression as a complication (Non-Patent Document 3). It is also reported that 60% of patients with vascular dementia had depression symptoms and that 27% had depression as a complication (Non-Patent Document 4). In other words, it is pointed out that since senile depression may progress to dementia, depression is a risk factor of dementia including Alzheimer's disease (Non-Patent Document 5). Hence, as a pharmaceutical which is effective against not only Alzheimer's disease but also depression symptoms, a compound which inhibits the activity of AChE, which is an enzyme that decomposes acetylcholine, and also inhibits serotonin transporter (SERT) binding has been developed (Non-Patent Document 6). However, in order to be capable of inhibiting SERT, it is necessary that the inhibitor have at least a structure for entering the three-dimensional structure of SERT, and likewise, in order to be capable of inhibiting AChE, the inhibitor is required to have a structure for entering the three-dimensional structure of AChE. Since SERT and AChE are completely different in structure, it is very unlikely that an inhibitor compound having inhibitory activity against either of SERT and AChE, if found, will have inhibitory activity against the other as well. A methodology for searching for such a dual inhibitor requires the steps of synthesizing and developing candidate compounds by joining together structures resembling the respective two types of inhibitors, and of verifying them to see whether they actually have such dual inhibitory activity (supra).

Besides, there is a concern that long-term ingestion of an artificially synthesized compound which people have little experience in eating may cause critical side effects on the human body.

It has been reported that a dipeptide-related compound as food affects the cerebral function (for example: Patent Document 1). There is a report showing that Cyclo(Pro-Gly) causes a change in the membrane potential in synaptoneurosome and, therefore, has memory improving effect (Non-Patent Document 7). Another report shows that β-alanyl-histidine (carnosine) reduces spontaneous activity in an open-field experiment and, therefore, has memory improving action (Non-Patent Document 8). On the other hand, it is also reported that β-alanyl-leucine, β-alanyl-isoleucine and carnosine have spontaneous activity promoting action (Patent Document 2). Accordingly, while one report shows that carnosine reduces spontaneous activity, another report shows that carnosine promotes spontaneous activity; no agreed opinion has been formed, yet. Further, there is a report showing that Cyclo(His-Pro) reduces spontaneous activity and, therefore, has memory improving action (Non-Patent Document 9). However, from the fact that Cyclo(His-Pro) reduces the spontaneous activity, it is difficult to conclude that Cyclo(His-Pro) has memory improving action. In fact, it has not been confirmed that Cyclo(His-Pro) has memory improving action. Further, it is reported that Tyr-Leu exhibits anxiolytic-like activity via activation of serotonin 5-$HT_{1A}$, dopamine $D_1$ and $GABA_A$ (Non-Patent Document 10).

As described above, some dipeptide-related compounds are discovered to have certain effect on the cerebral function. However, there has been no such a report showing that by improving depression symptoms, progress of dementia is prevented or learning and memory are improved.

CITATION LIST

Patent Documents

Patent Document 1: Japanese Unexamined Patent Application Publication No. 2012-517998
Patent Document 2: Japanese Patent Public Disclosure No. 2008-255087

Non-Patent Documents

Non-Patent Document 1: Neurochem. Int. 32, 413-419, 1998

Non-Patent Document 2: Pharmaceuticals and Medical Devices Agency, Japan, Review Report (common name: donepezil), Jul. 10, 2007

Non-Patent Document 3: Am J Psychiatry 146(5), 577-87, 1989

Non-Patent Document 4: Arch Neurol. 44(4), 389-93, 1987

Non-Patent Document 5: J Neurol Neurosurg Psychiatry 75, 1662-1666, 2004

Non-Patent Document 6: Chem Pharm Bull 58(3), 273-287, 2010

Non-Patent Document 7: Bulletin of Experimental Biology and Medicine 135(6), 559-562, 2003

Non-Patent Document 8: Proceeding of 53rd ICoMST, 375-376, 2007

Non-Patent Document 9: Acta Pharmaceutica Sinica, 26(7), 546-547, 1991

Non-Patent Document 10: FEBS Letters 584, 599-604, 2010

SUMMARY OF INVENTION

Technical Problem

If a component which inhibits AChE activity and SERT binding is found from foods that we eat regularly, it can be expected that dementia and depression symptoms will be improved significantly safely and effectively. In other words, if daily depressive symptoms can be improved and development of dementia can be retarded, development of dementia will be prevented and, furthermore, in a case of Alzheimer's disease with a complication of depression, it can be expected that the reduced ability to learn and memorize will be improved. Further, there is a high social demand for as much retardation as possible of learning and memory disorders associated with aging that are seen in an amnestic syndrome such as loss of memory in daily life even when illness is not developed. Hence, there has been a demand for a food-derived component which is safe, can be ingested for a long period of time and inhibits SERT binding and AChE activity.

The present invention aims to provide antidementia agents which are free from the problem of side effects and are excellent in safety. The present invention also aims to provide agents for improving learning and memory which are useful for improvement of learning and memory and can be ingested continuously.

Solution to Problem

As a result of extensive and intensive efforts made to solve the problems stated above, the present inventors have found that 2,5-piperazinedione,3,6-bis(phenylmethyl)-,(3S, 6S) found in food had antidepressive action because it had inhibitory activity on SERT binding, increased the concentration of serotonin in the prefrontal region, and showed a significant dose-dependent reduction in the escape latency in a Morris water maze test using mice in a depressive state. The present inventors also found that 2,5-piperazinedione, 3,6-bis(phenylmethyl)-,(3S,6S) also had learning and memory improving action because it inhibited the activity of acetylcholine esterase, increased the concentration of acetylcholine in the hippocampus which is most intimately related to learning and memory, and increased the percentage of correct choices in a radial maze test using rats with scopolamine-induced impairment of learning which were commonly used as a dementia animal model. The above findings led to the completion of the present invention.

Namely, the present invention is not limited but directed to [1] to [8] shown below.

[1] An antidementia agent comprising 2,5-piperazinedione, 3,6-bis(phenylmethyl)-,(3S,6S) as an active ingredient

[2] The antidementia agent of [1], which improves a symptom of Alzheimer type dementia or retards the progress of a symptom of Alzheimer type dementia.

[3] The antidementia agent of [1] or [2], which also has antidepressive action.

[4] The antidementia agent of [3], which improves a depressive symptom or retards the progress of a depressive symptom.

[5] The antidementia agent of [1], which also has learning motivation improving action.

[6] The antidementia agent of any one of [1] to [5], which is for oral administration.

[7] An agent for improving learning and memory, comprising 2,5-piperazinedione,3,6-bis(phenylmethyl)-,(3S,6S) as an active ingredient.

[8] The agent for improving learning and memory of [7], which improves a symptom of Alzheimer type dementia or retards the progress of a symptom of Alzheimer type dementia.

[9] The agent for improving learning and memory of [7] or [8], which is for oral administration.

Advantageous Effects of Invention

The present invention provides antidementia agents and agents for improving learning and memory, each comprising 2,5-piperazinedione,3,6-bis(phenylmethyl)-,(3S,6S) as an active ingredient. The agents of the present invention not only have the effect of preventing progress of dementia as well as antidepressive effect and learning motivation improving action, but also have prophylactic/therapeutic effect on dementia because the agents improve reduced learning and memory in dementia. Furthermore, the agents of the present invention are extremely safe and, thus, long-term administration is possible.

DESCRIPTION OF EMBODIMENTS

Figure 1:
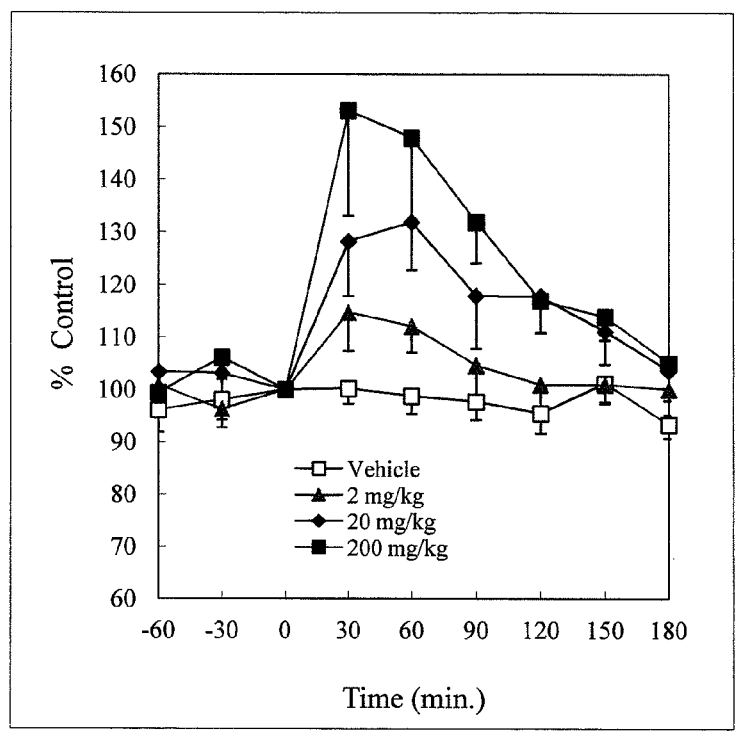
FIG. 1 shows the concentration of serotonin in the prefrontal region of normal rats which were orally administered with 2,5-piperazinedione,3,6-bis(phenylmethyl)-,(3S,6S) for 2 weeks.

A detailed explanation will be given below for the embodiments of the present invention.

Antidementia Agent and Agent for Promoting Learning and Memory

The present invention is directed to an antidementia agent which contains 2,5-piperazinedione,3,6-bis(phenylmethyl)-,(3S,6S) as an active ingredient, and an agent for improving learning and memory which contains 2,5-piperazinedione,3,6-bis(phenylmethyl)-,(3S,6S) as an active ingredient.

The agents of the present invention contain 2,5-piperazinedione,3,6-bis(phenylmethyl)-,(3S,6S) as an active ingredient, improve depressive symptoms, have learning motivation improving action, prophylactic/therapeutic effect on an amnestic syndrome which is a learning and memory disorder associated with aging, and prophylactic/therapeutic effect on various types of dementia including Alzheimer type dementia, and have the effect of preventing progress of dementia by improving depression symptoms which are risk factors of dementia. In other words, the active ingredient of the agents of the present invention has antidepressive action, learning motivation improving action, antidementia action, and learning and memory promoting action.

At present, selective serotonin reuptake inhibitors (SSRI) and serotonin/noradrenaline reuptake inhibitors (SNRI) as well as tricyclic antidepressants and tetracyclic antidepressants are clinically introduced as therapeutic drugs or prophylactic drugs for depression. SSRI and SNRI are antidepressants which are significantly improved in side effects of conventional tricyclic antidepressants. It is known that SSRI improves depression symptoms by inhibiting SERT binding and reuptake of serotonin through the synaptic cleft to thereby increase the concentration of serotonin in the synaptic cleft. The active ingredient of the agents of the present invention inhibits SERT binding.

Inhibitory activity on SERT binding may be measured by, for example, a method described in a published document (Eur J Pharmacol, 368, 277-283, 1999). Namely, it is measured by determining whether $^3$H-labeled imipramine binds to human SERT expressed in CHO cells.

The active ingredient of the agents of the present invention has the effect of increasing the concentration of serotonin in the synaptic cleft via inhibitory activity on SERT binding. When the concentration of serotonin in the prefrontal region of normal rats which were orally administered with 2,5-piperazinedione,3,6-bis(phenylmethyl)-,(3S,6S) for 2 weeks was measured by microdialysis, it was confirmed that the concentration of serotonin was increased dose-dependently and significantly.

The active ingredient of the agents of the present invention has antidepressive action. Antidepressive action as SSRI may be measured by a method described in a published document (Exp Anim, 59(2), 191-197, 2010). Specifically, first, a Morris water maze test is conducted for 8 days using mice. Then, the mice which could not reach an escape platform within 60 seconds are chosen ("loser mice"; referred to as "inferior" in the above document). The loser mice were orally administered with the active ingredient of the present invention, i.e., 2,5-piperazinedione,3,6-bis(phenylmethyl)-,(3S,6S), prior to a Morris water maze test, resulting in a dose-dependent, significant reduction in the escape latency; from this result it was confirmed that the active ingredient of the present invention had antidepressive action.

The active ingredient of the agents of the present invention has learning motivation improving action. The Morris water maze test has been reported as a method for measuring spatial memory and learning (Learn. Motiv. 12, 239-260 (1981)). In this test, the time required to reach an escape platform (escape latency) is used as a parameter for evaluation, because mice will remember their surrounding scenery and swim in a pool filled with water to try to find and reach the escape platform, which is a goal, with their memory as a guide. Since mice used in a main test are chosen from those which were subjected to the Morris water maze test for 8 days and could not reach the escape platform within 60 minutes, a reduction in the time required to reach the escape platform can be regarded as an improvement in learning motivation. Loser mice were orally administered with the active ingredient of the present invention, i.e., 2,5-piperazinedione,3,6-bis(phenylmethyl)-,(3S,6S), prior to a Morris water maze test, resulting in a dose-dependent, significant reduction in the escape latency; from this result it was confirmed that the active ingredient of the present invention had antidepressive action.

The active ingredient of the agents of the present invention has AChE inhibitory action. AChE inhibitory action may be measured with MATP+ (1,1-dimethyl-4-acetylthiomethylpiperidine), which is a substrate having high selectivity for AChE (Biol Pharma Bull, 33(4), 702-706, 2010). Specifically, AChE is reacted with MATP+, and measurement is conducted using as an indicator a change in absorbance at 412 nm associated with reaction of detection reagent DNTB (5,5'-dithiobis(2-nitrobenzoic acid)). The concentration ($IC_{50}$) of the active ingredient of the agents of the present invention, i.e., 2,5-piperazinedione,3,6-bis(phenylmethyl)-,(3S,6S), required for 50% inhibition of AChE activity is 3.4 µM.

It is considered that the hippocampus region of the brain, in which a cholinergic neuron is known to be involved, has a function related to learning and memory. Since cholinergic neuron is impaired in degenerative disease with symptoms such as reduced learning and memory, an increase in the concentration of acetylcholine in the hippocampus will improve the symptoms such as reduced learning and memory. The concentration of acetylcholine in the rat hippocampus was increased about 2.5-fold, as measured by microdialysis, by the active ingredient of the agents of the present invention.

Scopolamine is a non-selective competitive antagonist of muscarinic acetylcholine receptors. Laboratory animals with scopolamine-induced impairment of learning are widely used as a memory disorder model. The active ingredient of the agents of the present invention significantly improved the percentage of correct choices in a radial maze test using rats with scopolamine-induced impairment of learning, showing that the active ingredient of the agents of the present invention had learning and memory promoting action.

The active ingredient of the agents of the present invention, i.e., 2,5-piperazinedione,3,6-bis(phenylmethyl)-,(3S,6S), is an antidepressant (agent for preventing progress of dementia) or a learning and memory promoting agent (agent for treating dementia) excellent in safety which exhibits no toxicity even when 2 g/kg is administered in a single-dose acute toxicity test using mice, shows a no-observable-effect level of 10 mg/kg/day or more in a 28-day repeated-dose toxicity test using rats, and exhibits no mutagenicity in an Ames test, a chromosome aberration test and a mice micronucleus test.

The active ingredient 2,5-piperazinedione,3,6-bis(phenylmethyl)-,(3S,6S) may be a commercially-available synthetic reagent, but an ingredient extracted from a naturally occurring product is more preferred for use in terms of safety. To obtain from a naturally occurring product, a process comprising the following steps can be presented as an example:

(1) a pretreatment step in which meat of livestock or poultry, fish meat or shellfish meat is used as a starting material and heated in a liquid to remove water-soluble proteins contained therein;

(2) a heating step in which the liquid is replaced after the pretreatment and heating is repeated again; and (3) a filtration step in which the obtained liquid sample is filtered.

A preferred starting material used in the above pretreatment step (1) is a naturally occurring product rich in active ingredient, i.e., 2,5-piperazinedione,3,6-bis(phenylmethyl)-, (3S,6S), particularly meat of livestock or poultry, fish meat, or shellfish meat. Examples of meat of livestock or poultry include meat of livestock, i.e., cattle, pig, horse, sheep or goat, meat of non-livestock animals such as wild boar or deer, meat of poultry, i.e., chicken, turkey, quail, domestic duck or crossbred duck, as well as meat of non-poultry wild birds such as wild duck, pheasant, sparrow or thrush. Likewise, it is also possible to use fish meat and shellfish meat which are eaten in the course of a normal diet. As other examples, plant materials such as coffee and cocoa can also be used. Among these examples for meat of livestock or poultry, fish meat and shellfish meat, chicken meat is preferred for use because 2,5-piperazinedione,3,6-bis(phenylmethyl)-,(3S,6S) can be efficiently obtained at high concentrations.

In the pretreatment step (1), any treatment for reducing water-soluble proteins contained in meat of livestock may be performed, for example, by boiling in water at 100° C. to 160° C. for 30 minutes to several hours (preferably about 3 to 8 hours). As a heating device, a pressure cooker, an autoclave and so on can be combined for use depending on the intended conditions.

The heating step (2) is preferably accomplished at a high temperature under a high pressure (100° C. or more and 1 atm or more), for example, at 100° C. or more, and more preferably at 120° C. or more. As a heating device, a pressure cooker, an autoclave and so on can also be combined for use depending on the intended conditions.

The pretreatment step (1) and the heating step (2) may be performed continuously as a single step. Alternatively, the pretreatment step may be followed by removal of the meat of livestock and then replacement of the liquid before the starting material is subjected to the heating step. Since samples with lower Brix values can be obtained when liquid replacement is performed after the pretreatment step (1) and before the heating step (2), it is more desirable to conduct the steps (1) and (2) as separate steps.

It should be noted that heat treatment in the steps (1) and (2) is preferably performed in a solvent in order to prevent plant and animal materials from burning. Examples of a solvent preferred for use include water, ethanol, or mixtures thereof. Namely, a plant or animal material containing proteins is mixed with a solvent and subjected to heat treatment, followed by collection of the solvent to obtain a solution rich in 2,5-piperazinedione,3,6-bis(phenylmethyl)-, (3S,6S). The concentration of 2,5-piperazinedione,3,6-bis (phenylmethyl)-,(3S,6S) can be quantified in various manners, for example, by high performance liquid chromatography (HPLC).

The resulting solution containing 2,5-piperazinedione,3, 6-bis(phenylmethyl)-,(3S,6S) may be used directly as the agent of the present invention or, if necessary, may be purified or concentrated to further increase the concentration of the active ingredient. Concentration may be accomplished by using an evaporator or by lyophilization, etc.

In the filtration step, the power of filtration may be determined as appropriate, depending on the form of the agent, and the filtration step may be accomplished in a manner well known to those skilled in the art.

The antidementia agent and agent for improving learning and memory of the present invention may be supplemented as appropriate with additives such as carriers, excipients, stabilizers, antioxidants, antiseptics, surfactants, etc. The precise dosage varies depending on the disease, the severity of disease, age, sex, body weight and so on and may be determined as appropriate. In the case of humans, for example, the active ingredient is given several times a day at a dose of 0.002 to 20 mg/kg per administration. It is preferably given one to three times a day, but the period of administration is not limited in any way.

Although the route of administration may be oral or parenteral, oral dosage forms are preferred in terms of easy administration. Oral dosage forms may be in any form including tablets, capsules, powders, granules, solutions, elixirs, etc. Moreover, in the case of oral dosage forms, the active ingredient is generally formulated into the intended form such as tablets with or without excipients. Examples of excipients used for this purpose include gelatin, saccharides (e.g., lactose, glucose), starches (e.g., wheat starch, rice starch, corn starch), fatty acid salts (e.g., calcium stearate, magnesium stearate), talc, vegetable oils, alcohols (e.g., stearyl alcohol, benzyl alcohol), gum, polyalkylene glycols, etc.

In general, these oral dosage forms comprise the active ingredient at a content of, for example, 0.01 to 80% by weight, preferably 0.01 to 60% by weight. In the case of solutions, suspensions or syrups comprising the active ingredient at a content of 0.01 to 20% by weight can be presented as examples. Carriers used in this case are water-soluble excipients such as flavorings, syrups, pharmaceutical micelles and the like.

The antidementia agent and agent for improving learning and memory of the present invention will be further described in more detail by way of the following examples, which are not intended to limit the present invention.

EXAMPLES

[Example 1] Inhibitory Activity on SERT Binding

SERT inhibitory activity was measured in accordance with a published document (Eur J Pharmacol, 368, 277-283, 1999) by determining whether $^3$H-labeled imipramine bound to human SERT expressed in CHO cells. As a result, it was found that 2,5-piperazinedione,3,6-bis(phenylmethyl)-,(3S,6S) inhibited human SERT binding. The concentration ($IC_{50}$) of 2,5-piperazinedione,3,6-bis(phenylmethyl)-,(3S,6S) required for 50% inhibition of human SERT binding was 8.1 μM.

[Example 2] Effect on the Concentration of Serotonin in the Prefrontal Region of Rats Male SD rats which were 10 to 12 weeks of age were used. The concentration of serotonin in the prefrontal region of each rat was measured in accordance with a published document (Kehr J., and Yoshitake T. (2006) Monitoring brain chemical signals by microdialysis. In: Encyclopedia of Sensors, Vol. 6. (Eds. C. A. Grimes, E. C. Dickey and M. V. Pishko) American Scientific Publishers, USA. 287-312) by microdialysis. Specifically, a dialysis probe was implanted in the prefrontal region of each rat under isoflurane anesthesia. Five days after the implantation surgery, artificial cerebrospinal fluid (148 mM of NaCl, 4 mM of KCl, 0.8 mM of $MgCl_2$, 1.4 mM of $CaCl_2$, 1.2 mM of $Na_2HPO_4$, 0.3 mM of $NaH_2PO_4$, pH 7.2)) was perfused at the flow rate of 1 µl/min under ambulatory conditions without anesthesia. 2,5-Piperazinedione,3,6-bis(phenylmethyl)-,(3S,6S) was suspended in 0.5% sodium carboxymethylcellulose (CMC-Na), and 2 mg/kg, 20 mg/kg, and 200 mg/kg were orally administered for 14 consecutive days. The amount of acetylcholine in 15 µl of perfusion liquid collected immediately before the final oral administration and every 30 minutes after the oral administration was quantitatively determined by HPLC-ECD. The results obtained within the period from 1 hour before the oral administration to 3 hours after the oral administration are shown in FIG. 1, where the time immediately before the oral administration of the test sample is set to 0 minute. As a result, the concentration of serotonin in the prefrontal region was increased significantly by the oral administration of 20 mg/kg and 200 mg/kg of 2,5-piperazinedione,3,6-bis(phenylmethyl)-,(3S,6S).

[Example 3] Effect on Morris Water Maze Test

Figure 2:
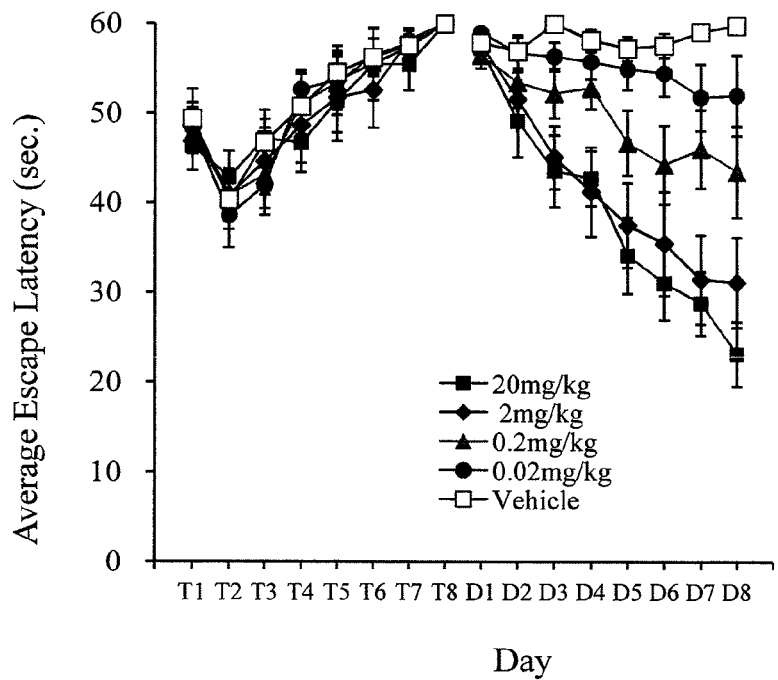
FIG. 2 shows the latency to an escape platform in a Morris water maze in the case in which mice in a depressive state were orally administered with 2,5-piperazinedione,3,6-bis (phenylmethyl)-,(3S,6S).

Antidepressive action was measured in accordance with a published document (Exp Anim, 59(2), 191-197, 2010). Specifically, water at a temperature of 22±1° C. was poured into a cylindrical tank having a diameter of 90 cm and a height of 35 cm to give a water depth of 20 cm, and an escape platform having a diameter of 10 cm was placed in the tank. Titanium oxide was added to the water in the tank so that the water became opaque to thereby hide the position of the escape platform. First, a Morris water maze test was conducted for 8 days using male C57BL/6 mice which were 10 to 11 weeks of age, and the mice which could not reach the escape platform within 60 seconds were chosen ("loser mice"; referred to as "inferior" in the above document). Next, 2,5-piperazinedione,3,6-bis(phenylmethyl)-,(3S,6S) was suspended in 0.5% CMC-Na, and 0.02 mg/kg, 0.2 mg/kg, 2 mg/kg, and 20 mg/kg were orally administered before a Morris water maze test. As a result, the escape latency was reduced dose-dependently by the oral administration of 2,5-piperazinedione,3,6-bis(phenylmethyl)-,(3S,6S), and the escape latency was reduced significantly by the oral administration of 0.2 mg/kg or more (FIG. 2). The foregoing results showed that 2,5-piperazinedione,3,6-bis(phenylmethyl)-,(3S,6S) had antidepressive action and learning motivation improving action.

[Example 4] AChE Inhibitory Action

AChE inhibitory action was measured with MATP+ (1,1-dimethyl-4-acetylthiomethylpiperidine), which is a substrate having high selectivity for AChE (Biol Pharma Bull, 33(4), 702-706, 2010). Specifically, AChE was reacted with MATP+, and measurement was conducted using as an indicator a change in absorbance at 412 nm associated with reaction of detection reagent DNTB (5,5'-dithiobis(2-nitrobenzoic acid)). As a result, the concentration ($IC_{50}$) of 2,5-piperazinedione,3,6-bis(phenylmethyl)-,(3S,6S) required for 50% inhibition of AChE was 3.4 µM.

Figure 3:
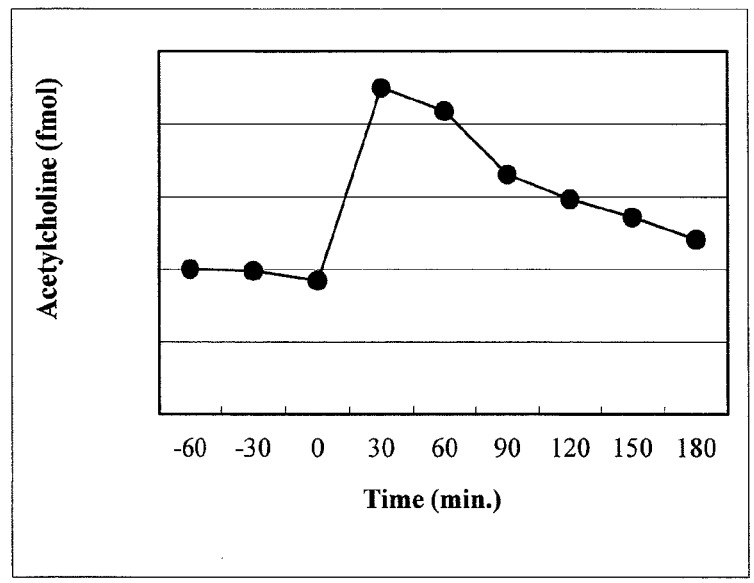
FIG. 3 shows the concentration of acetylcholine in the hippocampus of normal rats which were orally administered with 2,5-piperazinedione,3,6-bis(phenylmethyl)-,(3S,6S).

[Example 5] Effect on the Concentration of Acetylcholine in the Hippocampus of Rats A dialysis probe was embedded in the hippocampus of each rat, and measurement was conducted as in Example 1. 2,5-Piperazinedione,3,6-bis(phenylmethyl)-,(3S,6S) was suspended in 0.5% CMC-Na, and 200 mg/kg was orally administered once. The amount of acetylcholine in 15 µl of perfusion liquid collected immediately before the final oral administration and every 30 minutes after the oral administration was quantitatively determined by HPLC-ECD. The results obtained within the period from 1 hour before the oral administration to 3 hours after the oral administration are shown in FIG. 3, where the time immediately before the oral administration of the test sample is set to 0 minute. As a result, the concentration of acetylcholine in the hippocampus was increased 2.5-fold by the oral administration of 200 mg/kg of 2,5-piperazinedione,3,6-bis(phenylmethyl)-,(3S,6S).

Figure 4:
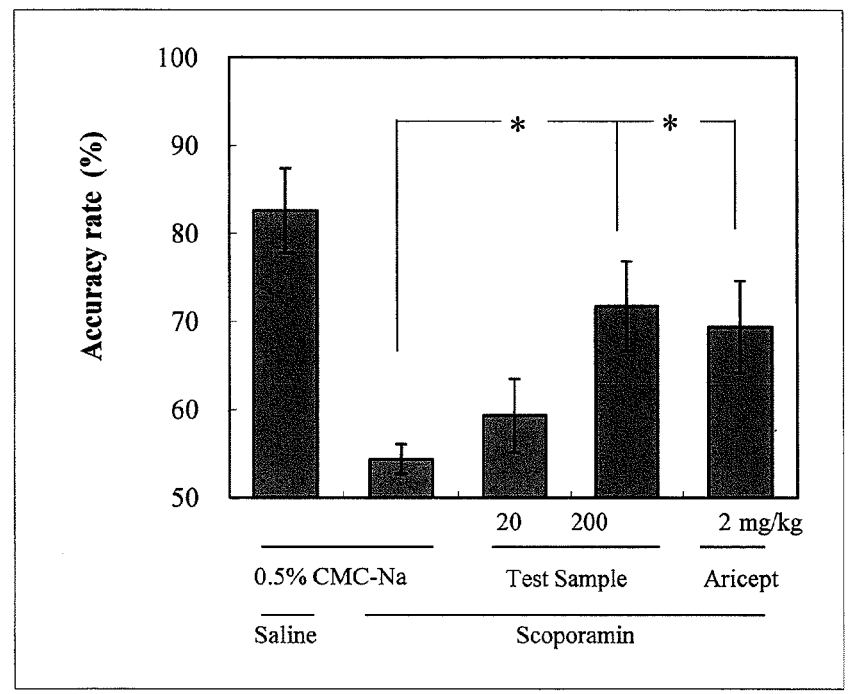
FIG. 4 shows the percentage of correct choices in a radial maze test using rats with scopolamine-induced impairment of learning in the case in which the rats were allowed to learn in advance and then orally administered with 2,5-piperazinedione,3,6-bis(phenylmethyl)-,(3S,6S).

[Example 6] Radial Maze Test Using Rats with Scopolamine-Induced Impairment of Learning Using SD male rats which were 7 weeks of age, practice training was conducted while the rats were under food deprivation, and thereafter a main test was conducted.
Practice Training
Food was placed at the end of each arm of an 8-direction radial maze, and an animal was placed on a platform at the center of the maze. Completion of one trial was when the animal finished acquiring food from all arms or when 10 minutes elapsed since the animal was placed on the platform. The training was conducted once a day. "Correct choice" was defined as visiting an unselected arm in the trial, and "wrong choice" was defined as visiting an arm from where food had already been acquired. A trial in which 7 out of first 8 choices were correct choices was defined as a standard trial, and the training was conducted until this result was achieved in three consecutive trials.
Main Test
2,5-Piperazinedione,3,6-bis(phenylmethyl)-,(3S,6S) was suspended in 0.5% CMC-Na, and 20 mg/kg and 200 mg/kg were orally administered to the rats which attained the standard in the above practice training trials. Ten minutes after the oral administration, 0.5 mg/kg of scopolamine was intraperitoneally administered. Thirty minutes after the intraperitoneal administration of scopolamine, an 8-direction radial maze test was conducted, and the number of wrong choices and the time taken for the mice to acquire all food were counted. As a positive control, 2 mg/kg of donepezil hydrochloride (Aricept) was orally administered in place of the test sample. The results of the percentage of correct choices in the trials which were completed when 5 minutes elapsed or when the mice ate all food which had been placed on the 8 arms are shown in FIG. 4. As a result, the percentage of correct choices was improved significantly by the oral administration of 200 mg/kg of 2,5-piperazinedione,3,6-bis(phenylmethyl)-,(3S,6S). The foregoing results showed that 2,5-piperazinedione,3,6-bis(phenylmethyl)-,(3S,6S) had learning and memory improving action.

INDUSTRIAL APPLICABILITY

The present invention provides antidementia agents and agents for improving learning and memory which contain 2,5-piperazinedione,3,6-bis(phenylmethyl)-,(3S,6S) as an active ingredient. The antidementia agents and agents for improving learning and memory of the present invention are not only excellent in their effects, but are also extremely safe, and are further suitable for use in foods and beverages because they are tasteless and odorless and have a white color in purified form.

The invention claimed is:

1. A method for improving or retarding the progress of a symptom of Alzheimer type dementia, comprising administering to a subject in need thereof an agent comprising 2,5-piperazinedione-3,6-bis(phenylmethyl)-,(3S,6S).

2. The method according to claim 1, wherein the symptom is depression.

3. The method according to claim 1, wherein the symptom is reduced learning motivation.

4. The method according to claim 1, wherein the agent is administered orally.

5. A method for improving learning and memory in a subject having Alzheimer type dementia, comprising administering to a subject in need thereof an agent comprising 2,5-piperazinedione-3,6-bis(phenylmethyl)-,(3S,6S).

6. The method according to claim 5, wherein the agent is administered orally.

* * * * *